United States Patent
Naito et al.

(10) Patent No.: US 10,231,688 B2
(45) Date of Patent: Mar. 19, 2019

(54) RADIATION IMAGE ANALYSIS DEVICE, METHOD, AND PROGRAM

(71) Applicant: FUJIFILM Corporation, Tokyo (JP)

(72) Inventors: Satoshi Naito, Ashigarakami-gun (JP); Takahiro Kawamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 635 days.

(21) Appl. No.: 14/868,725

(22) Filed: Sep. 29, 2015

(65) Prior Publication Data

US 2016/0089104 A1     Mar. 31, 2016

(30) Foreign Application Priority Data

Sep. 30, 2014   (JP) .................. 2014-199996

(51) Int. Cl.
*A61B 6/00*        (2006.01)
*A61B 8/08*        (2006.01)

(52) U.S. Cl.
CPC ............ *A61B 6/547* (2013.01); *A61B 6/4417* (2013.01); *A61B 6/588* (2013.01); *A61B 6/5294* (2013.01); *A61B 8/0858* (2013.01)

(58) Field of Classification Search
CPC ....... A61B 6/547; A61B 6/4417; A61B 6/588; A61B 6/5294
See application file for complete search history.

(56) References Cited

FOREIGN PATENT DOCUMENTS

JP      2007-44134 A     2/2007
WO     WO 2009/142166 A1     11/2009

*Primary Examiner* — Tse Chen
*Assistant Examiner* — Joanne Hoffman
(74) *Attorney, Agent, or Firm* — Birch, Stewart, Kolasch & Birch, LLP

(57) ABSTRACT

The distance between the radiation source and an object (SOD value) is acquired, distance dependent information which is obtained from a radiation image and changes with the distance between a radiation source and a radiation detector (SID value) is acquired, a temporary thickness of the object is determined by a first function representing the correspondence relationship of first information having at least one piece of the distance dependent information, the SID value, and the thickness of the object, and the temporary SID value is determined by adding the SOD value to the determined value. The thickness of the object is determined by a second function representing the correspondence relationship of second information having at least one piece of the distance dependent information, the SID value, and the thickness of the object, and the SID value is determined by adding the SOD value to the determined value.

11 Claims, 3 Drawing Sheets

RADIATION IMAGE ANALYSIS DEVICE, METHOD, AND PROGRAM

CROSS-REFERENCE TO RELATED APPLICATIONS

The present application claims priority under 35 U.S.C. § 119 to Japanese Patent Application No. 2014-199996, filed on Sep. 30, 2014, all of which are hereby expressly incorporated by reference into the present application.

BACKGROUND OF THE INVENTION

1. Field of the Invention

The present invention relates to a radiation image analysis device, a method, and a program which determine the distance between a radiation source and a radiation detector using information obtained from a radiation image obtained by imaging an object.

2. Description of the Related Art

In the field of radiation imaging, the distance (source-image distance (SID)) between a radiation source and a radiation detector is an important parameter which is used when determining the actual size of an object from the size of an object image obtained as a radiation image by radiography, when performing image processing, such as scattered radiation elimination processing, on the captured radiation image, or the like. For this reason, various methods of determining the SID have been hitherto suggested. For example, JP2007-44134A suggests a method which captures a radiation image with an exposure field narrowed by a collimator and calculates an SID based on the ratio of the width of an exposure field in the radiation detector determined from the radiation image and the diaphragm width of the collimator. Furthermore, PCT Japanese Patent Domestic Re-Publication No. WO2009-142166A suggests a method which determines both the distance (source-object distance (SOD)) between a radiation source and an object surface and an object thickness by actual measurement and adds the distance and the object thickness to obtain an SID. Furthermore, a method which, in a state where an object does not exist between a radiation exposure unit and a radiation image detector, directly measures an SID by an ultrasonic range finder attached to the radiation exposure unit is known.

SUMMARY OF THE INVENTION

However, according to the method of JP2007-44134A, imaging needs to be executed by adjusting the relative positional relationship of the radiation source, the collimator, and the radiation detector such that the boundary of the exposure field by the collimator falls within the detection surface of the radiation detector. Meanwhile, for example, when the detection surface is hidden by an object, the positional relationship between the detection surface and the boundary of the exposure field by the collimator cannot be confirmed, and the adjustment of the positional relationship is difficult. Furthermore, according to the method of PCT Japanese Patent Domestic Re-Publication No. WO2009-142166A, there is a problem in that the object thickness needs to be measured manually and it is time consuming for a person imaging. Furthermore, according to the method which directly measures the SID by the ultrasonic range finder, when an object exists between the radiation exposure unit and the radiation image detector, there is a problem in that measurement light is obstructed by the object, and the distance to the radiation detector cannot be measured.

In consideration of the situations described above, the invention provides a radiation image analysis device, a method, and a non-transitory computer-readable recording medium having a program recorded thereon capable of automatically and stably determining the distance (SID) between a radiation source and a radiation detector.

A radiation image analysis device of the invention includes a source-object distance acquisition unit that acquires the distance between a radiation source and an object, an information acquisition unit that acquires at least one piece of distance dependent information, which is obtained from a radiation image captured by exposure of radiation from the radiation source to the object and changes with an SID value indicating the distance between the radiation source and a radiation detector, a first object thickness calculation unit that determines a temporary thickness of the object by assigning, to a first function representing the correspondence relationship of first information having at least one piece of information out of the distance dependent information acquired by the information acquisition unit, the SID value, and the thickness of the object in a radiation exposure direction, the distance between the radiation source and the object acquired by the source-object distance acquisition unit as the SID value and information corresponding to the first information acquired by the information acquisition unit as the first information, a first source-detector distance calculation unit that determines a temporary SID value by adding the distance between the radiation source and the object acquired by the source-object distance acquisition unit to the temporary thickness of the object determined by the first object thickness calculation unit, a second object thickness calculation unit that determines the thickness of the object by assigning, to a second function representing the correspondence relationship of second information having at least one piece of information out of the distance dependent information acquired by the information acquisition unit, the SID value, and the thickness of the object in the radiation exposure direction, the temporary SID value determined by the first source-detector distance calculation unit as the SID value and information corresponding to the second information acquired by the information acquisition unit as the second information, and a second source-detector distance calculation unit that calculates a second source-detector distance by adding the distance between the radiation source and the object acquired by the source-object distance acquisition unit to the thickness of the object determined by the second object thickness calculation unit.

Here, examples of the distance dependent information which is obtained from the radiation image and changes with the distance between the radiation source and the radiation detector include the received dose of radiation exposed from the radiation source, transmitted through the object, and reaching the radiation detector, the length of an image of a specific intra-object structure in a predetermined reference direction on the radiation image, or the like. For example, as information of the received dose, the received dose at one point or a plurality of points on the radiation detector is acquired. Furthermore, as the length of the image of the intra-object structure, the length of the image in a predetermined reference direction associated with the structure in advance for one structure or each of a plurality of intra-object structures is acquired.

The first information and the second information may be the same information or may be different kinds of information. When the first information and the second information are the same information, the first function and the second function may be the same function or may be different functions.

As described above, the first function and the second function are a function which indicates the correspondence relationship of the SID value and the thickness of the object in the radiation exposure direction using the first information or the second information. When creating such a function, for example, if the first or second information is the length of a certain bone of a human body as an object on a radiation image, a function which includes, as variables, the actual length of the bone and the ratio of the distance between the surface of the human body on the radiation detector side and the bone to the thickness of the human body in the radiation exposure direction can be created. In this case, it is assumed that the variables have known values. In this way, the first function and the second function may further include variables other than three variables of the SID value, the thickness of the object in the radiation exposure direction, and the first or second information.

The source-object distance acquisition unit can acquire the distance between the radiation source and one point or each of a plurality of points on the surface of the object, that is, one value or a plurality of values as the "distance between the radiation source and the object". The first source-detector distance calculation unit and the second source-detector distance calculation unit calculate the SID value (or the temporary SID value) using one representative value determined based on one value acquired by the source-object distance acquisition unit or a plurality of values acquired by the source-object distance acquisition unit as the "distance between the radiation source and the object". The first object thickness calculation unit determines the temporary thickness of the object using one representative value determined based on one value acquired by the source-object distance acquisition unit or a plurality of values acquired by the source-object distance acquisition unit, or a plurality of values (the distance between the radiation source and each of a plurality of points on the surface of the object) acquired by the source-object distance acquisition unit as the "distance between the radiation source and the object" according to the content of the first function.

In the radiation image analysis device of the invention, the information acquisition unit may acquire, as one piece of the distance dependent information, a received dose of radiation exposed from the radiation source, transmitted through the object, and reaching the radiation detector, and one or both of the first function and the second function may be a function which represents the correspondence relationship of
(1) the SID value,
(2) the thickness of the object in the radiation exposure direction,
(3) a radiation attenuation coefficient of the object,
(4) an exposure dose of radiation exposed from the radiation source, and
(5) the received dose acquired by the information acquisition unit.

In the radiation image analysis device of the invention, the information acquisition unit may acquire, as one piece of the distance dependent information, the length of an image of a specific intra-object structure in a reference direction set in advance on the radiation image, and one or both of the first function and the second function may be a function which represents the correspondence relationship of
(1) the SID value,
(2) the thickness of the object in the radiation exposure direction,
(3) the ratio of the distance between the surface of the object on the radiation detector side and the specific intra-object structure to the thickness of the object in the radiation exposure direction,
(4) the length of the specific intra-object structure in a direction corresponding to the reference direction perpendicular to the radiation exposure direction, and
(5) the length of an image of the specific intra-object structure acquired by the information acquisition unit.

In the radiation image analysis device of the invention, the second function may be a function which is capable of calculating the thickness of the object with higher accuracy than the first function and is different from the first function.

In the radiation image analysis device of the invention, the first object thickness calculation unit may determine the temporary thickness of the object by assigning, to the first function, a value obtained by adding an object thickness correction value set in advance to the distance between the radiation source and the object acquired by the source-object distance acquisition unit as the SID value.

Here, as the object thickness correction value, for example, the standard thickness of the object can be set in advance. For example, when an object is a certain region of a human body, the thickness of the same region in a human body of a standard type can be set in advance. Furthermore, as the object thickness correction value, the average value, the minimum value, or the like of the thickness of the object measured within a given period in the past may be set in advance.

A radiation image analysis method of the invention includes a source-object distance acquisition process for acquiring the distance between a radiation source and an object, an information acquisition process for acquiring at least one piece of distance dependent information, which is obtained from a radiation image captured by exposure of radiation from the radiation source to the object and changes with an SID value indicating the distance between the radiation source and a radiation detector, a first object thickness calculation process for determining a temporary thickness of the object by assigning, to a first function representing the correspondence relationship of first information having at least one piece of information out of the distance dependent information acquired by the information acquisition process, the SID value, and the thickness of the object in a radiation exposure direction, the distance between the radiation source and the object acquired by the source-object distance acquisition process as the SID value and information corresponding to the first information acquired by the information acquisition process as the first information, a first source-detector distance calculation process for determining a temporary SID value by adding the distance between the radiation source and the object acquired by the source-object distance acquisition process to the temporary thickness of the object determined by the first object thickness calculation process, a second object thickness calculation process for determining the thickness of the object by assigning, to a second function representing the correspondence relationship of second information having at least one piece of information out of the distance dependent information acquired by the information acquisition process, the SID value, and the thickness of the object in the radiation exposure direction, the temporary SID value determined by the first source-detector distance calculation process as the SID value and information corresponding to the second information acquired by the information acquisition process as the second information, and a second source-detector distance calculation process for calculating a second source-detector distance by adding the distance between the radiation source and the object acquired by the source-object distance acquisition process to the thickness of the object determined by the second object thickness calculation process.

A radiation image analysis program of the invention causes a computer to function as a source-object distance acquisition unit that acquires the distance between a radiation source and an object, an information acquisition unit that acquires at least one piece of distance dependent information, which is obtained from a radiation image captured by exposure of radiation from the radiation source to the object and changes with an SID value indicating the distance between the radiation source and a radiation detector, a first object thickness calculation unit that determines a temporary thickness of the object by assigning, to a first function representing the correspondence relationship of first information having at least one piece of information out of the distance dependent information acquired by the information acquisition unit, the SID value, and the thickness of the object in a radiation exposure direction, the distance between the radiation source and the object acquired by the source-object distance acquisition unit as the SID value and information corresponding to the first information acquired by the information acquisition unit as the first information, a first source-detector distance calculation unit that determines a temporary SID value by adding the distance between the radiation source and the object acquired by the source-object distance acquisition unit to the temporary thickness of the object determined by the first object thickness calculation unit, a second object thickness calculation unit that determines the thickness of the object by assigning, to a second function representing the correspondence relationship of second information having at least one piece of information out of the distance dependent information acquired by the information acquisition unit, the SID value, and the thickness of the object in the radiation exposure direction, the temporary SID value determined by the first source-detector distance calculation unit as the SID value and information corresponding to the second information acquired by the information acquisition unit as the second information, and a second source-detector distance calculation unit that calculates a second source-detector distance by adding the distance between the radiation source and the object acquired by the source-object distance acquisition unit to the thickness of the object determined by the second object thickness calculation unit.

The radiation image analysis program of the invention normally has a plurality of program modules, and the function of each unit is realized by one program module or a plurality of program modules. The program module group is recorded on a recording medium, such as a compact disc-read only memory (CD-ROM) or a digital versatile disc (DVD), or is recorded on a storage attached to a server computer or a network storage in a downloadable state and provided to a user.

According to the radiation image analysis device, the method, and the program of the invention, the distance between the radiation source and the object is acquired, at least one piece of the distance dependent information which is obtained from the radiation image captured by exposure of radiation from the radiation source to the object and changes with the SID value indicating the distance between the radiation source and the radiation detector is acquired, the temporary thickness of the object is determined by assigning, to the first function representing the correspondence relationship of the first information having at least one piece of information out of the distance dependent information acquired by the distance dependent information acquisition process, the SID value, and the thickness of the object in the radiation exposure direction, the acquired distance between the radiation source and the object as the SID value and information corresponding to the first information acquired by the information acquisition process as the first information, the temporary SID value is determined by adding the distance between the radiation source and the object to the determined temporary thickness of the object, the thickness of the object is determined by assigning, to the second function representing the correspondence relationship of the second information having at least one piece of information out of the distance dependent information by the distance dependent information acquisition process, the SID value, and the thickness of the object in the radiation exposure direction, the determined temporary SID value as the SID value and information corresponding to the second information acquired by the information acquisition process as the second information, and the SID value is determined by adding the acquired distance between the radiation source and the object to the determined thickness of the object. Therefore, even when an object exists between the radiation exposure unit and the radiation image detector, the thickness of the object and the distance between the radiation source and the radiation detector are determined sequentially and repeatedly using the distance dependent information obtained from the radiation image and the distance between the radiation source and the object, whereby it is possible to automatically determine the distance between the radiation source and the radiation detector with high accuracy.

DESCRIPTION OF THE PREFERRED EMBODIMENTS

Figure 1:
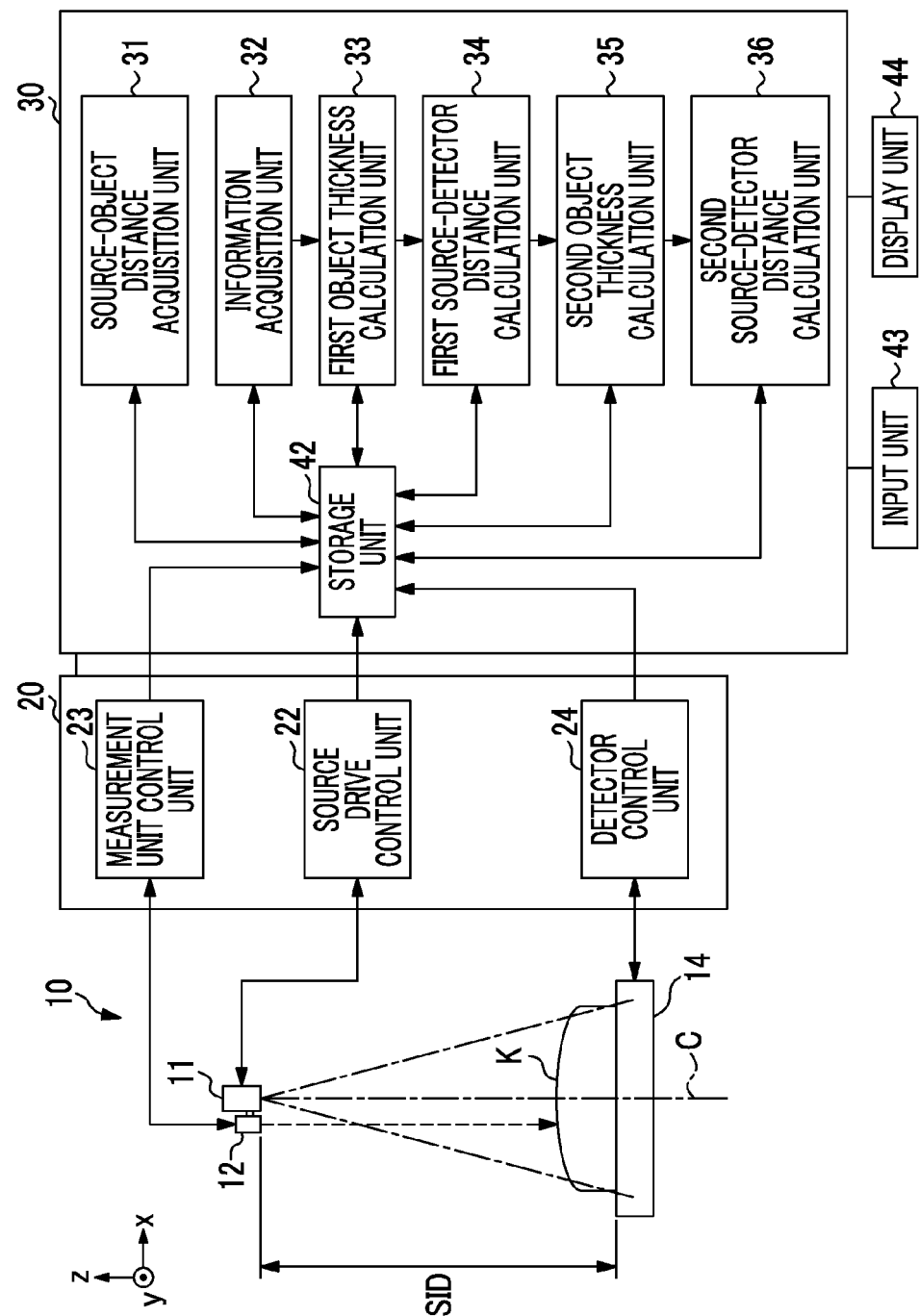
FIG. 1 is a diagram showing the schematic configuration of a radiation image processing system provided with an embodiment of the invention.

Hereinafter, an embodiment of the invention will be described referring to the drawings. FIG. 1 is a schematic block diagram showing the configuration of a radiation image processing system provided with an embodiment of the invention. As shown in FIG. 1, the radiation image processing system includes an imaging device 10, a control device 20 which controls the system, and an image analysis device 30 (radiation image analysis device).

The imaging device 10 includes a radiation source 11 which exposes an object K to radiation, a radiation detector 14 which detects radiation transmitted through the object K to acquire a radiation image of the object K, and a distance measurement unit 12 which is attached to the radiation source 11 and measures the distance between the radiation source and the object.

The distance measurement unit 12 is constituted of, a range finder, such as an ultrasonic sensor attached to the radiation source 11, and measures the distance between the radiation source 11 and one point or each of a plurality of points on the surface of the object K. Here, the distance measurement unit 12 is positioned at a measurement position deviated by several cm in an X-axis direction from the radiation source 11 in a side portion of the radiation source 11 through an attachment member, and measures the distance between the measurement position and one point or each of a plurality of points on the surface of the object K. In this way, the distance between the radiation source and the object is not limited to the strict distance between the radiation source and the object, and may be recognized as being substantially equal to the distance between the radiation source and the object. It is desirable that the distance measurement unit 12 positions a measurement position as close to the radiation source as possible. As the distance between the radiation source and the object, when measuring the distance between the radiation source 11 and one point on the surface of the object K, the distance between the measurement position and the surface of the object K may be measured substantially in parallel with an optical axis C.

The control device 20 includes a radiation source drive control unit 22 which controls driving of the radiation source 11 according to set imaging conditions, a detector control unit 24 which controls the radiation detector 14, acquires the radiation image of the object K, and stores the radiation image in a storage unit 42, and a measurement unit control unit 23 which controls the distance measurement unit 12. The measurement unit control unit 23 detects a detection signal from the distance measurement unit 12 connected thereto by a signal line, calculates distance information according to the detection signal, and transmits the distance information to a source-object distance acquisition unit 31 of the image analysis device 30.

The image analysis device 30 is a computer including an input unit 43 which receives various inputs from an operator on the image analysis device 30, a display unit 44, a central processing unit (CPU), a semiconductor memory, a communication interface, and a storage unit 42, such as a hard disk or a solid state drive (SSD), and a radiation image analysis program according to the embodiment of the invention is installed on the image analysis device 30. With the execution of the radiation image analysis program, the central processing unit and the memory of the image analysis device 30 cooperatively function as a source-object distance acquisition unit 31, an information acquisition unit 32, a first object thickness calculation unit 33, a first source-detector distance calculation unit 34, a second object thickness calculation unit 35, and a second source-detector distance calculation unit 36. The input unit 43 is constituted of, a keyboard, a mouse, a touch panel, and the like. The input unit 43 receives various inputs from the operator on the image analysis device 30. The display unit 44 is constituted of a cathode ray tube (CRT) or a liquid crystal display, and performs the display of the radiation image acquired from the radiation detector 14 or the display of information necessary for other kinds of desired processing.

The source-object distance acquisition unit 31 acquires the distance between the radiation source 11 and one point or each of a plurality of points on the surface of the object K measured by the distance measurement unit 12 from the storage unit 42.

The information acquisition unit 32 acquires at least one piece of distance dependent information which is obtained from the radiation image of the object K and changes with the distance between the radiation source 11 and the radiation detector 14. As the distance dependent information, for example, the received dose of radiation exposed from the radiation source 11, transmitted through the object K, and reaching the radiation detector 14, the length of an image of a specific intra-object structure in a predetermined reference direction on the radiation image, and the like are acquired.

At this time, as the received dose, the received dose at one point (for example, an intersection point with the optical axis C) or each of a plurality of points on the radiation detector is acquired. The received dose at each position on the radiation detector can be acquired based on the pixel value of a pixel of the radiation image corresponding to the position.

As the length of the image of the intra-object structure, the length of the image in a predetermined reference direction associated with the structure is acquired for one structure or each of a plurality of structures. For example, when an object is a breast of a human body, for one bone or each of a plurality of bones selected from a breastbone, a collarbone, a backbone, and a rib, the length of the image of the bone in a predetermined direction on the radiation image is acquired. For example, if an intra-object structure is a collarbone, the length of the image of the collarbone in a longitudinal direction or a direction on the radiation image corresponding to a direction substantially orthogonal to the longitudinal direction can be acquired.

The first object thickness calculation unit 33 determines the temporary thickness of the object K by assigning, to a first function representing the correspondence relationship of first information having at least one piece of information out of distance dependent information acquired by the information acquisition unit 32, the SID value as the distance between the radiation source and the radiation detector, and the thickness of the object in the radiation exposure direction, the distance between the radiation source 11 and the object K acquired by the source-object distance acquisition unit 31 as the SID value and information corresponding to the first information acquired by the information acquisition unit 32 as the first information.

As the first function, for example, functions A to E illustrated below can be used.

<Function A>

The function A determines the value of the thickness T in the object K by Expression (1) described below, and the value is set as the temporary thickness of the object K. The function of Expression (1) described below represents the correspondence relationship of the SID value, a received dose Ik (first information) of radiation exposed from the radiation source, transmitted through the object, and reaching the radiation detector, the thickness T of the object in the radiation exposure direction, a radiation attenuation coefficient μ of the object, and an exposure dose Io of radiation exposed from the radiation source.

$$I_k = \frac{I_o}{SID^2} \times \exp(-T \times \mu) \tag{1}$$

The value of the thickness T of the object is determined by assigning, to the function of Expression (1) described above, the distance between the radiation source 11 and the object K acquired by the source-object distance acquisition unit 31 as the SID value, the received dose at one point (for example, the intersection point with the optical axis C) on the radiation detector 14 acquired by the information acquisition unit 32 as the received dose Ik and values acquired in advance and stored in the storage unit 42 as the radiation attenuation coefficient μ and the exposure dose Io, and is set as the temporary thickness of the object K.

At this time, as the radiation attenuation coefficient μ, a value corresponding to the object K can be acquired with reference to an attenuation coefficient of each type of object published in J. H. Hubbell and S. M. Seltzer, Tables of X-Ray Mass Attenuation Coefficients and Mass Energy-Absorption Coefficients from 1 keV to 20 MeV for Elements Z=1 to 92 and 48 Additional Substances of Dosimetric Interest. Physical Reference Data (NISTIR 5632), NIST, (1996) or the like. When an object is a human body, alternatively, an acrylic block (experimental model) having the same thickness as an average thickness of a human body is imaged under the same imaging conditions as actual imaging, and the value of an attenuation coefficient may be determined from a thus-determined attenuation ratio of radiation.

The exposure dose Io is a value corresponding to the received dose obtained when imaging is performed under the same imaging conditions as actual imaging in a state where an object does not exist, and can be calculated based on a tube voltage and an imaging dose (mAs value) at the time of imaging.

<Function B>

Figure 2:
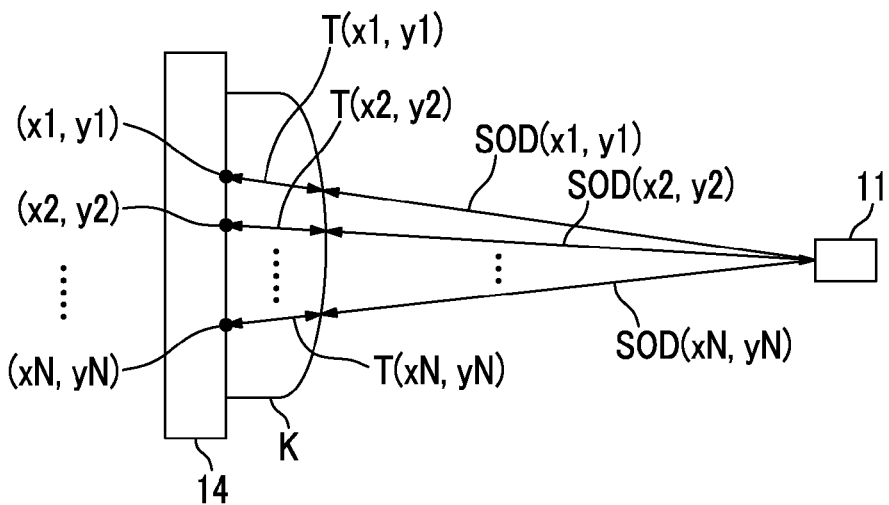
FIG. 2 is a diagram (first view) illustrating an object thickness calculation method.

For example, as shown in FIG. 2, the function B determines the values of the thickness T(x1,y1) to T(xN,yN) of the object on a radiation exposure line toward a plurality of respective positions (xi,yi) (where i=1 to N) on the detection surface of the radiation detector 14 by Expression (2), and sets one representative value (for example, an average value, a median value, a mode value, a maximum value, a minimum value, or the like) based on the values as the temporary thickness of the object K. The function of Expression (2) described below represents the correspondence relationship of the SID value, the received dose Ik(xi,yi) (first information) of radiation reaching the position (xi,yi) on the detection surface of the radiation detector 14, the thickness T(xi,yi) of the object, the radiation attenuation coefficient μ of the object, and the exposure dose Io(xi,yi) of radiation exposed from the radiation source to the position (xi,yi) on the detection surface of the radiation detector 14.

$$I_k(x_i, y_i) = \frac{I_o(x_i, y_i)}{SID^2} \times \exp(-\mu \times T(x_i, y_i)) \quad (2)$$

For each of a plurality of positions (xi,yi) (where i=1 to N), the value of the thickness T(xi,yi) of the object is determined by assigning, to the function of Expression (2) described above, the distance SOD(xi,yi) between the radiation source 11 and the object K on the radiation exposure line toward the position (xi,yi) on the detection surface of the radiation detector 14 acquired by the source-object distance acquisition unit 31 as the SID value, the received dose at the position (xi,yi) on the detection surface of the radiation detector 14 acquired by the information acquisition unit 32 as the received dose Ik(xi,yi), and values acquired in advance and stored in the storage unit 42 as the radiation attenuation coefficient μ and the exposure dose Io(xi,yi). Then, one representative value (average value or the like) is determined based on all determined values of the thickness T(x1,y1) to T(xN,yN) of the object, and is set as the temporary thickness of the object K. At this time, it is assumed that an attenuation coefficient of the object K and the exposure dose Io(xi,yi) calculated based on the tube voltage and the imaging dose (mAs value) at the time of imaging are acquired in advance and stored in the storage unit 42.

<Function C>

The function C is a function which determines the values of the thickness T(x1,y1) to T(xM,yM) of the object on the radiation exposure line toward each of a plurality of positions (xj,yj) (where j=1 to M) on the detection surface of the radiation detector 14 by Expression (3) described below and sets one representative value (for example, an average value, a median value, a mode value, a maximum value, a minimum value, or the like) determined based on the values as the temporary thickness of the object K. The function of Expression (3) described below represents the correspondence relationship of the SID value, the received dose Ik(xi,yi) (first information) of radiation reaching the position (xi,yi) on the detection surface of the radiation detector 14, the thickness T(xj,yj) of the object on the radiation exposure line toward each of a plurality of positions (xj,yj) (where j=1 to M) on the detection surface of the radiation detector 14 including the position (xi,yi), the radiation attenuation coefficient μ of the object, the exposure dose Io(xj,yj) of radiation exposed from the radiation source to each of a plurality of positions (xj,yj) on the detection surface of the radiation detector 14, the distance Dij between the position (xi,yi) and each of a plurality of positions (xj,yj), and the tube voltage V at the time of imaging. Here, PSF(Dij,T(xj,yj),V) is a function representing a spread distribution of scattered radiation at the pixel position (xi,yi).

$$I_k(xi, yi) = \sum_{xj,yj} \frac{Io(xj, yj)}{SID^2} \times \exp(-\mu \times T(xj, yj)) \times PSF(Dij, T(xj, yj), V) \quad (3)$$

For each of a plurality of positions (xi,yi) (where i=1 to N), the values of the thickness T(x1,y1) to T(xM,yM) of the object are determined by solving, using a simplex method, a gradient method, or the like, a simultaneous equation obtained by assigning, to the function of Expression (3) described above, the distance SOD(xi,yi) between the radiation source 11 and the object K on the radiation exposure line toward the position (xi,yi) on the detection surface of the radiation detector 14 acquired by the source-object distance acquisition unit 31 as the SID value, the received dose at the position (xi,yi) on the detection surface of the radiation detector 14 acquired by the information acquisition unit 32 as the received dose Ik(xi,yi), the values acquired in advance and stored in the storage unit 42 as the radiation attenuation coefficient μ, the tube voltage V, and the exposure dose Io(xj,yj), and the value of the distance calculated from the coordinates of the position (xi,yi) and the coordinates of the position (xj,yj) as the distance Dij. Then, one representative value (average value or the like) is determined based on the values, and is set as the temporary thickness of the object K. At this time, it is assumed that the attenuation coefficient of the object K, the tube voltage at the time of imaging, and the exposure dose Io(xj,yj) calculated based on the tube voltage and the imaging dose (mAs value) at the time of imaging are acquired in advance and stored in the storage unit 42.

<Function D>

Figure 3:
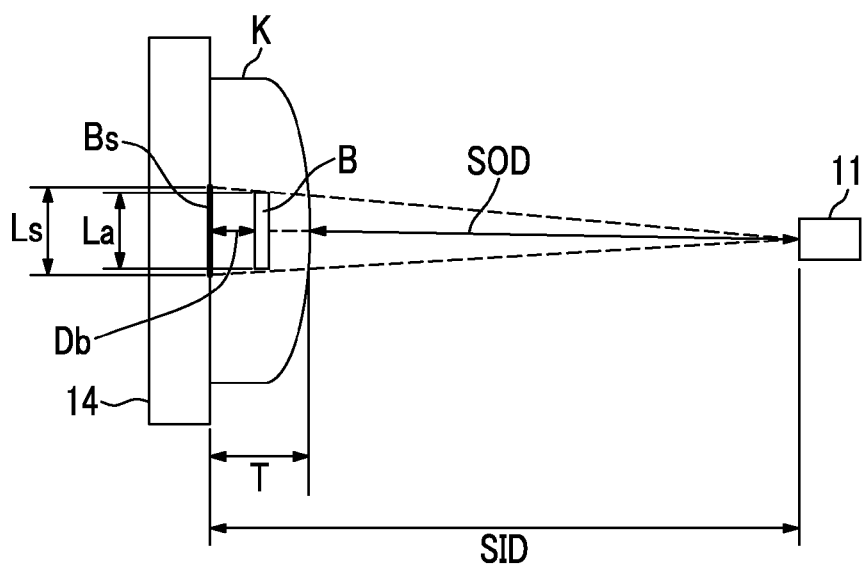
FIG. 3 is a diagram (second view) illustrating an object thickness calculation method.

For example, as shown in FIG. 3, the function D determines the value of the thickness T of the object based on the relationship of the distance between the radiation source 11 and the radiation detector 14 and a magnification ratio of an image of a specific intra-object structure B by Expressions (4) and (5) described below, and sets the value as the temporary thickness of the object K. The function of Expression (4) described below represents the correspondence relationship of a length La of the intra-object structure B in a reference direction (in the example shown in FIG. 3, an up-down direction of the paper surface) set in advance perpendicular to the radiation exposure direction, a length Ls (first information) of the image of the intra-object structure B in a direction corresponding to the reference direction on the radiation image, the SID value, and a distance Db between the surface of the object K on the radiation detector 14 side and the intra-object structure B in the radiation exposure direction, and the function of Expression (5) described below represents the correspondence relationship of the distance Db, the radio r of the distance between the surface of the object K on the radiation detector 14 side and the intra-object structure B to the thickness T of the object in the radiation exposure direction, and the thickness T of the object.

$$\frac{Ls}{La} = \frac{SID}{(SID - Db)} \quad (4)$$

$$Db = r \times T \quad (5)$$

First, the distance Db is determined by assigning, to the function of Expression (4) described above, the distance between the radiation source 11 and the object K acquired by the source-object distance acquisition unit 31 as the SID value, the length of the image of the intra-object structure B in the set reference direction on the radiation image acquired by the information acquisition unit 32 as the length Ls, and the value of the length of the intra-object structure B acquired in advance and stored in the storage unit 42 as the length La. Next, the value of the thickness T of the object is determined by assigning, to the function of Expression (5) described above, the determined distance Db and the value of a ratio r acquired in advance and stored in the storage unit 42, and the value is set as the temporary thickness of the object K.

At this time, the length Ls is not limited to the strict length of the intra-object structure B of the object K, and may be recognized as a value substantially corresponding to the length of the intra-object structure B, for example, the average length of the intra-object structure B or the like. Similarly, the ratio r may be recognized substantially as a value corresponding to the strict ratio of the distance between the surface of the object K on the radiation detector 14 side and the intra-object structure B to the thickness T of the object in the radiation exposure direction.

<Function E>

The function E determines the value of the thickness T(Bk) of the object based on the magnification ratio of the image of the intra-object structure for each of a plurality of intra-object structures Bk (where k=1 to K) captured in the radiation image by Expressions (6) and (7) described below, and sets one representative value (for example, an average value, a median value, a mode value, a maximum value, a minimum value, or the like) determined based on the values as the temporary thickness of the object K. The function of Expression (6) described below represents the correspondence relationship of a length La(Bk) of the intra-object structure Bk in the reference direction set in advance perpendicular to the radiation exposure direction, a length Ls(Bk) (first information) of the image of the intra-object structure Bk in a direction corresponding to the reference direction on the radiation image, the SID value, and a distance Db(Bk) between the surface of the object K on the radiation detector 14 side and the intra-object structure Bk in the radiation exposure direction, and the function of Expression (7) described below represents the correspondence relationship of the distance Db(Bk), a ratio r(Bk) of the distance between the surface of the object K on the radiation detector 14 side and the intra-object structure Bk to the thickness T of the object in the radiation exposure direction, and a thickness T(Bk) of the object on the radiation exposure line passing through the intra-object structure Bk.

$$\frac{Ls(Bk)}{La(Bk)} = \frac{SID}{(SID - Db(Bk))} \quad (6)$$

$$Db(Bk) = r(Bk) \times T(Bk) \quad (7)$$

For each of a plurality of intra-object structures Bk (where k=1 to K), first, the distance Db(Bk) is determined by assigning, to the function of Expression (6) described above, the distance between the radiation source 11 and the object K on the radiation exposure line passing through the intra-object structure Bk acquired by the source-object distance acquisition unit 31 as the SID value, the length of the image of the intra-object structure Bk in the set reference direction on the radiation image acquired by the information acquisition unit 32 as the length Ls(Bk), and the value of the length of the intra-object structure Bk acquired in advance and stored in the storage unit 42 as the length La(Bk). Next, the value of the thickness T(Bk) of the object is determined by assigning, to the function of Expression (7) described above, the determined distance Db(Bk) and the ratio r(Bk) acquired in advance and stored in the storage unit 42. Then, one representative value (average value or the like) is determined based on all determined values of the thickness T(B1) to T(Bk) of the object, and is set as the temporary thickness of the object K.

The first object thickness calculation unit 33 may determine the temporary thickness of the object K by one function of the functions A to E illustrated above, but may determine the average value of the thickness of the object acquired by each of two or more functions among the functions A to E and may set the average value as the temporary thickness of the object K.

The first source-detector distance calculation unit 34 determines a temporary SID value by adding the distance between radiation source 11 and one point (for example, an intersection point with the optical axis C) on the surface of the object K acquired by the source-object distance acquisition unit 31 to the temporary thickness of the object K determined by the first object thickness calculation unit 33. When the distance between the radiation source 11 and each of a plurality of points on the surface of the object K is acquired in the source-object distance acquisition unit 31, one representative value determined based on the distance between the radiation source 11 and each point of a plurality of points on the surface of the object K, instead of the distance to one point, may be added to determine the temporary SID value.

The second object thickness calculation unit 35 determines the thickness of the object K by assigning, to a second function representing the correspondence relationship of the second information having at least one piece of information out of the distance dependent information acquired by the information acquisition unit 32, the SID value as the distance between the radiation source and the radiation detector, and the thickness of the object in the radiation exposure direction, the temporary SID value determined by the first source-detector distance calculation unit 34 as the SID value and information corresponding to the second information acquired by the information acquisition unit 32 as the second information.

As the second function, for example, the functions A to E illustrated in the description of the first object thickness calculation unit 33 can be used. A difference is only that, in the first object thickness calculation unit 33, the distance between the radiation source 11 and the object K acquired by the source-object distance acquisition unit 31 is assigned to each of the functions A to E as the SID value; however, in the second object thickness calculation unit 35, the temporary SID value determined by the first source-detector distance calculation unit 34 is assigned to each of the functions A to E as the SID value. Similarly to the first object thickness calculation unit 33, the second object thickness calculation unit 35 may determine the thickness of the object K by one function of the functions A to E illustrated above, but may determine the average value of the thickness of the object acquired by each of two or more functions among the functions A to E and may set the average value as the thickness of the object K.

As the second function, when a function which is capable of calculating the thickness of the object with higher accuracy than the first function and is different from the first function is used, it is possible to reduce the time relating to the processing while maintaining SID value calculation with high accuracy. For example, in the functions A to C, the influence of more variables is considered in an order of the function C>the function B>the function A, and it can be said that the thickness of the object can be calculated with higher accuracy. Therefore, when the function A is used as the first function, the function B or the function C can be used as the second function, and when the function B is used as the first function, the function C can be used as the second function. In the functions D and E, the influence of more variables is considered in an order of the function E>the function D, and it can be said that the thickness of the object can be calculated with higher accuracy. Therefore, when the function D is used as the first function, the function E can be used as the second function.

The second source-detector distance calculation unit 36 determines the SID value by adding the distance between the radiation source 11 and one point (for example, an intersection point with the optical axis C) on the surface of the object K acquired by the source-object distance acquisition unit 31 to the thickness of the object K determined by the second object thickness calculation unit 35. When the distance between the radiation source 11 and each of a plurality of points on the surface of the object K is acquired in the source-object distance acquisition unit 31, the SID value may be determined by adding one representative value determined based on the distance between the radiation source 11 and each of a plurality of points on the surface of the object K, instead of the distance to one point.

Figure 4:
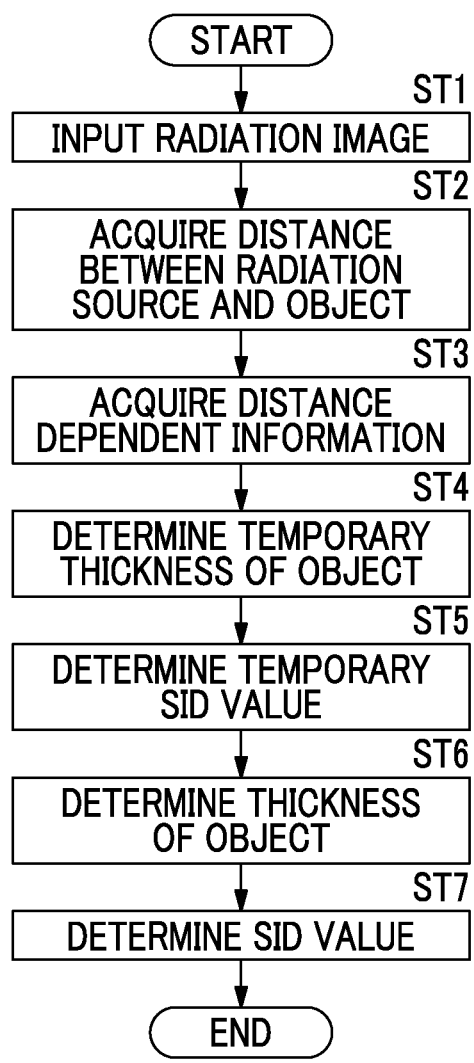
FIG. 4 is a flowchart showing the flow of processing which is performed by an image analysis device.

Next, the flow of processing which is performed by the image analysis device 30 will be described referring to the flowchart shown in FIG. 4. First, the radiation image of the object K acquired in the imaging device 10 is input to the image analysis device 30 (Step ST1). Then, the source-object distance acquisition unit 31 acquires the distance between the radiation source 11 and one point or each of a plurality of points on the surface of the object K measured by the distance measurement unit 12 of the imaging device 10 (Step ST2). Next, the information acquisition unit 32 acquires at least one piece of the distance dependent information, which changes with the distance between the radiation source 11 and the radiation detector 14, from the radiation image of the object K (Step ST3).

Next, the first object thickness calculation unit 33 determines the temporary thickness of the object K by assigning, to the first function representing the correspondence relationship of the first information having at least one piece of information out of the distance dependent information acquired in Step ST3, the SID value as the distance between the radiation source and the radiation detector, and the thickness of the object in the radiation exposure direction, the distance between the radiation source 11 and the object K acquired in Step ST2 as the SID value and information corresponding to the first information acquired in Step ST3 as the first information (Step ST4). At this time, as the first function, for example, the functions A to E described above can be used.

Next, the first source-detector distance calculation unit 34 determines the temporary SID value by adding the distance between the radiation source 11 and the object K acquired in Step ST2 to the temporary thickness of the object K determined in Step ST4 (Step ST5). Next, the second object thickness calculation unit 35 determines the thickness of the object K by assigning, to the second function representing the correspondence relationship of the second information having at least one piece of information out of the distance dependent information acquired in Step ST3, the SID value as the distance between the radiation source and the radiation detector, and the thickness of the object in the radiation exposure direction, the temporary SID value determined in Step ST5 as the SID value and information corresponding to the second information acquired in Step ST3 as the second information (Step ST6). At this time, as the second function, for example, each of the functions A to E described above can be used.

Finally, the second source-detector distance calculation unit 36 determines the SID value by adding the distance between the radiation source 11 and the object K acquired in Step ST2 to the thickness of the object K determined in Step ST6 (Step ST7), and ends the processing. The determined SID value is stored in the storage unit 42, and is provided for processing for determining the actual size of the object from the size of an object image obtained as a radiation image by radiography, scattered radiation elimination processing on the captured radiation image, processing for determining the thickness of the object, or the like.

With the above configuration, in the image analysis device 30 of this embodiment, the source-object distance acquisition unit 31 acquires the distance between the radiation source 11 and the object K, the information acquisition unit 32 acquires at least one piece of the distance dependent information which is obtained from the radiation image captured by exposure of radiation from the radiation source 11 to the object K and changes with the SID value as the distance between the radiation source 11 and the radiation detector 14, the first object thickness calculation unit 33 determines the temporary thickness of the object by assigning, to the first function representing the correspondence relationship of the first information having at least one piece of information out of the distance dependent information acquired by the information acquisition unit 32, the SID value, and the thickness of the object in the radiation exposure direction, the distance between the radiation source 11 and the object K acquired by the source-object distance acquisition unit 31 as the SID value and information corresponding to the first information acquired by the information acquisition unit 32 as the first information, and the temporary SID value is determined by adding the distance between the radiation source 11 and the object acquired by the source-object distance acquisition unit 31 to the determined temporary thickness of the object. The first source-detector distance calculation unit 34 determines the thickness of the object by assigning, to the second function representing the correspondence relationship of the second information having at least one piece of information out of the distance dependent information acquired by the information acquisition unit 32, the SID value, and the thickness of the object in the radiation exposure direction, the temporary SID value determined by the first object thickness calculation unit 33 as the SID value and information corresponding to the second information acquired by the information acquisition unit 32 as the second information, and the second object thickness calculation unit 35 determines the SID value by adding the distance between the radiation source and the object acquired by the source-object distance acquisition unit 31 to the thickness of the object determined by the first source-detector distance calculation unit 34. With this, even when an object exists between the radiation exposure unit and the radiation image detector, the thickness of the object and the distance between the radiation source and the radiation detector are determined sequentially and repeatedly using the distance dependent information obtained from the radiation image and the distance between the radiation source and the object, whereby it is possible to automatically determine the distance between the radiation source and the radiation detector with high accuracy.

In the foregoing embodiment, a case where the first object thickness calculation unit 33 determines the temporary thickness of the object by assigning, to the first function, the distance (SOD value) between the radiation source 11 and the object K acquired by the source-object distance acquisition unit 31 as the SID value has been described. However, the invention is not limited thereto, and the temporary thickness of the object may be determined by assigning a value obtained by adding an object thickness correction value set in advance to the SOD value as the SID value. Here, as the object thickness correction value, for example, the standard thickness of the object may be set in advance. For example, when an object is a certain region of a human body, the thickness of the same region in a human body of a standard type can be set in advance. Furthermore, as the object thickness correction value, alternatively, the average value, the minimum value, or the like of the thickness of the object measured within a given period in the past may be set in advance.

In the foregoing embodiment, although a case where a series of processing for determining the thickness of the object using the distance dependent information acquired from the radiation image and determining the SID value by adding the SOD value to the determined thickness of the object is repeatedly performed twice, and the SID value determined at the second time is set as the final SID value, the series of processing may be repeatedly performed three times or more, and the SID value determined last may be set as the final SID value.

What is claimed is:

1. A radiation image analysis device comprising:
a computer processor; and
a memory storing software which, when executed by the computer processor, performs a process including
acquiring the distance between a radiation source and an object;
acquiring at least one piece of distance dependent information, which is obtained from a radiation image captured by exposure of radiation from the radiation source to the object and changes with an SID value indicating the distance between the radiation source and a radiation detector;
determining a temporary thickness of the object by assigning, to a first function representing the correspondence relationship of first information having at least one piece of the distance dependent information acquired according to the process, the SID value, and the thickness of the object in a radiation exposure direction, the acquired distance between the radiation source and the object as the SID value and information corresponding to the first information acquired according to the process as the first information;
determining a temporary SID value by adding the acquired distance between the radiation source and the object to the determined temporary thickness of the object;
determining the thickness of the object by assigning, to a second function representing the correspondence relationship of second information having at least one piece of the distance dependent information acquired according to the process, by the information acquisition unit, the SID value, and the thickness of the object in the radiation exposure direction, the determined temporary SID value as the SID value and information corresponding to the second information acquired according to the process as the second information; and
calculating a second source-detector distance by adding the acquired distance between the radiation source and the object to the determined thickness of the object.

2. The radiation image analysis device according to claim 1,
wherein the process acquires, as one piece of the distance dependent information, a received dose of radiation exposed from the radiation source, transmitted through the object, and reaching the radiation detector, and
one or both of the first function and the second function are a function which represents the correspondence relationship of
(1) the SID value,
(2) the thickness of the object in the radiation exposure direction,
(3) a radiation attenuation coefficient of the object,
(4) an exposure dose of radiation exposed from the radiation source, and
(5) the received dose acquired according to the process.

3. The radiation image analysis device according to claim 1,
wherein the process acquires, as one piece of the distance dependent information, the length of an image of a specific intra-object structure in a reference direction set in advance on the radiation image, and
one or both of the first function and the second function are a function which represents the correspondence relationship of
(1) the SID value,
(2) the thickness of the object in the radiation exposure direction,
(3) the ratio of the distance between the surface of the object on the radiation detector side and the specific intra-object structure to the thickness of the object in the radiation exposure direction, (4) the length of the specific intra-object structure in a direction corresponding to the reference direction perpendicular to the radiation exposure direction, and (5) the length of an image of the specific intra-object structure acquired according to the process.

4. The radiation image analysis device according to claim 1, wherein the second function is a function which is capable of calculating the thickness of the object with higher accuracy than the first function and is different from the first function.

5. The radiation image analysis device according to claim 1, wherein the process determines the temporary thickness of the object by assigning, to the first function, a value obtained by adding an object thickness correction value set in advance to the distance between the radiation source and the object acquired according to the process as the SID value.

6. The radiation image analysis device according to claim 2, wherein the process determines the temporary thickness of the object by assigning, to the first function, a value obtained by adding an object thickness correction value set in advance to the distance between the radiation source and the object acquired according to the process as the SID value.

7. The radiation image analysis device according to claim 3, wherein the process determines the temporary thickness of the object by assigning, to the first function, a value obtained by adding an object thickness correction value set in advance to the distance between the radiation source and the object acquired according to the process as the SID value.

8. The radiation image analysis device according to claim 4, wherein the process determines the temporary thickness of the object by assigning, to the first function, a value obtained by adding an object thickness correction value set in advance to the distance between the radiation source and the object acquired according to the process as the SID value.

9. A radiation image analysis method using the radiation image analysis device according to claim 1, the method comprising:

a source-object distance acquisition step that acquires the distance between a radiation source and an object;

an information acquisition step that acquires at least one piece of distance dependent information, which is obtained from a radiation image captured by exposure of radiation from the radiation source to the object and changes with an SID value indicating the distance between the radiation source and a radiation detector;

a first object thickness calculation step that determines a temporary thickness of the object by assigning, to a first function representing the correspondence relationship of first information having at least one piece of the distance dependent information acquired by the information acquisition step, the SID value, and the thickness of the object in a radiation exposure direction, the acquired distance between the radiation source and the object as the SID value and information corresponding to the first information acquired by the information acquisition step as the first information;

a first source-detector distance calculation step that determines a temporary SID value by adding the acquired distance between the radiation source and the object to the determined temporary thickness of the object;

a second object thickness calculation step that determines the thickness of the object by assigning, to a second function representing the correspondence relationship of second information having at least one piece of the distance dependent information acquired by the information acquisition step, the SID value, and the thickness of the object in the radiation exposure direction, the determined temporary SID value as the SID value and information corresponding to the second information acquired by the information acquisition step as the second information; and a second source-detector distance calculation step that calculates a second source-detector distance by adding the acquired distance between the radiation source and the object to the determined thickness of the object.

10. A non-transitory computer-readable recording medium having a radiation image analysis program recorded thereon causing a computer processor to:

acquire the distance between a radiation source and an object;

acquire at least one piece of distance dependent information, which is obtained from a radiation image captured by exposure of radiation from the radiation source to the object and changes with an SID value indicating the distance between the radiation source and a radiation detector;

determine a temporary thickness of the object by assigning, to a first function representing the correspondence relationship of first information having at least one piece of the distance dependent information acquired by the processor, the SID value, and the thickness of the object in a radiation exposure direction, the acquired distance between the radiation source and the object as the SID value and information corresponding to the first information acquired by the computer processor as the first information;

determine a temporary SID value by adding the acquired distance between the radiation source and the object to the determined temporary thickness of the object;

determine the thickness of the object by assigning, to a second function representing the correspondence relationship of second information having at least one piece of the distance dependent information acquired by the computer processor, the SID value, and the thickness of the object in the radiation exposure direction, the determined temporary SID value as the SID value and information corresponding to the second information acquired by the computer processor as the second information; and calculate a second source-detector distance by adding the acquired distance between the radiation source and the object to the determined thickness of the object.

11. A system comprising:

the radiation image analysis device according to claim 1;

the radiation source;

an ultrasonic sensor coupled to the radiation source, which measures the distance between the radiation source and the object; and a radiation detector which captures the radiation image.

* * * * *